United States Patent [19]

Leviness et al.

[11] Patent Number: 5,811,469
[45] Date of Patent: Sep. 22, 1998

[54] SLURRY HYDROCARBON SYNTHESIS WITH DOWNCOMER FED PRODUCT FILTRATION (LAW552)

[75] Inventors: Stephen C. Leviness, Baton Rouge, La.; Charles J. Mart, Coppell, Tex.

[73] Assignee: Exxon Research and Engineering Company, Florham Park, N.J.

[21] Appl. No.: 851,866

[22] Filed: May 6, 1997

[51] Int. Cl.[6] .................................................. C07C 27/00
[52] U.S. Cl. ............................. 518/700; 502/21; 502/22; 502/53; 422/230; 422/231
[58] Field of Search .............................. 518/700; 502/21, 502/22, 53; 422/230, 231

[56] References Cited

U.S. PATENT DOCUMENTS 5,382,748  1/1995  Behrmann et al. ...................... 585/899
5,527,473  6/1996  Ackerman ............................... 210/767

Primary Examiner—Gary Geist
Assistant Examiner—Jafar Parsa
Attorney, Agent, or Firm—Jay Simon

[57] ABSTRACT

Hydrocarbon liquid products are filtered and removed from a three phase hydrocarbon synthesis slurry comprising gas bubbles and particulate catalyst solids in a hydrocarbon liquid, by circulating the slurry through a gas disengaging downcomer immersed in the slurry to a filtration zone external or internal of the reactor, and then back into the slurry in the reactor. The gas disengagement densifies the slurry which is passed across the filtration surface under high flow conditions, to reduce solids build up on the filter as filter cake. Circulation through the filtration zone occurs by gravity and hydrostatics due to slurry density differences. The downcomer may also be a gas and solids reducing downcomer.

15 Claims, 2 Drawing Sheets

SLURRY HYDROCARBON SYNTHESIS WITH DOWNCOMER FED PRODUCT FILTRATION (LAW552)

BACKGROUND OF THE DISCLOSURE

FIELD OF THE INVENTION

The invention relates to a slurry filtration process. More particularly, the invention relates to a process for filtering hydrocarbon liquid from a three phase hydrocarbon synthesis slurry comprising gas bubbles and particulate catalyst solids in a hydrocarbon liquid, wherein the slurry is fed through a hydrocarbon liquid filtration zone by means of a gas disengaging downcomer immersed in the slurry, so that it contacts the filter under flow conditions.

BACKGROUND OF THE INVENTION

Slurry hydrocarbon synthesis (HCS) processes are known. In a slurry HCS process a synthesis gas (syngas) comprising a mixture of $H_2$ and CO is bubbled up as a third phase through a slurry in a reactor in which the slurry liquid comprises hydrocarbon products of the synthesis reaction and the dispersed, suspended solids comprise a suitable Fischer-Tropsch type hydrocarbon synthesis catalyst. Reactors which contain such a three phase slurry are sometimes referred to as "bubble columns", as is disclosed in U.S. Pat. No. 5,348,982. Irrespective of whether the slurry reactor is operated as a dispersed or slumped bed, the mixing conditions in the slurry will typically be somewhere between the two theoretical conditions of plug flow and back mixed. The catalyst particles are typically kept dispersed and suspended in the liquid by the lifting action of the syngas bubbling up through the slurry and by hydraulic means. Mechanical means such as impellers and propellers and the like are not used, because they will quickly erode and also cause attrition of the catalyst particles. One or more vertical, gas disengaging downcomers may be used as hydraulic means to assist in maintaining more uniform catalyst dispersion, by providing a vertical catalyst circulation in the slurry, as is disclosed in U.S. Pat. No. 5,382,748. The slurry liquid comprises the liquid hydrocarbon products of the HCS reaction and must be separated from the catalyst particles and removed from the reactor for further processing and upgrading. This is typically accomplished by mechanical filtration in which the slurry is fed to one or more filters, either inside the slurry in the reactor or outside the reactor, which permit the liquid to pass through, but not the catalyst particles. U.S. Pat. No. 5,527,473 and patent publications EP 0609079, WO 93/16796 and WO 94/16807 all relate to helically wound wedge wire filters and the like, while WO 93/16795 discloses vertical or helically wound fine metal threads or sintered metal. None of these processes reduces the gas content of the slurry before it is filtered. Further, a filter cake of catalyst particles builds up on the filter surface which reduces the product filtration rate, thereby requiring more filters. Accordingly, there is a need for a filtration process in which at least some of the gas bubbles are removed from the slurry prior to filtration and preferably reduce catalyst particle filter cake build up.

SUMMARY OF THE INVENTION

The invention relates to a process for filtering hydrocarbon liquid from a three phase hydrocarbon synthesis (HCS) slurry comprising gas bubbles and particulate catalyst solids in the hydrocarbon liquid, wherein a gas disengaging downcomer feeds the slurry to and through a hydrocarbon liquid filtration zone under relatively high net flow conditions, in which it contacts and flows past a filter which separates the hydrocarbon liquid from the solids. The gas disengaging downcomer produces a gas reduced, densified slurry and passes it to the filtration zone either inside or outside the slurry reactor. The gas reduced and densified slurry flows past and contacts the filter under relatively high net flow conditions in a net single direction as filtration occurs. This reduces the buildup of catalyst particles as filter cake on the filtration surface of the filter, due to the shearing, scouring and removing action of the flowing slurry. If the filtration occurs within the reactor, the slurry in which the downcomer is immersed is the reactive HCS slurry and the filter is in the downcomer. In the context of the invention, the slurry from which a portion is removed and passed or circulated into and through the gas disengaging downcomer will be referred to as a "slurry body". Also in the context of the invention, "circulated" and "passed" are used synonymously with respect to slurry flow from the slurry body, through the downcomer and filtration zone and back into the slurry body. Further, the filtration zone is or may be part of the downcomer. The process comprises passing slurry into a gas disengaging zone in which gas bubbles are removed from the slurry to form a gas reduced slurry of increased density with respect to the slurry in the slurry body from which it was taken. The gas reduced, denser slurry is fed down through a downcomer conduit or tube and into and through a filtration zone in which it contacts a filter for separating the liquid hydrocarbon from the catalyst particles and returns back to the slurry body from which it was withdrawn. The downcomer conduit depends downwardly from the gas disengaging zone, which may be a simple upwardly opening cup. In one embodiment, the gas disengaging cup and downcomer conduit form a single unit in which the gas disengaging cup or zone is positioned on top of the downcomer conduit which depends downwardly from the gas disengaging zone. The gas disengaging zone or cup is located upstream of the downcomer entrance and, in one embodiment, is located in the slurry where the catalyst concentration is least. In most cases this will be near the top of the slurry. Simple gas disengaging downcomers of this type are disclosed in U.S. Pat. No. 5,382,748.

The slurry flowing through the downcomer contacts the filter under conditions of relatively high net flow in a single direction, compared to the prior art processes in which the filter is immersed directly in the reactive slurry in the reactor in which there is considerable turbulence, but essentially zero net slurry flow in any given direction. If the filter is positioned within a straight downcomer immersed in the main slurry body in the HCS reactor, the densified slurry flows down through the downcomer past the filter in a direction substantially parallel to the longitudinal axis of the filter and across the filtration surface, and exits the downcomer nearer to the bottom of the slurry body. In another embodiment, the downcomer may be generally "J" shaped in which it extends down and then curves upward. In this embodiment the filter may be positioned in either the shorter or upward extending portion, or in the longer downward extending portion. These same considerations apply in the cases where the downcomer feeds the gas reduced, densified slurry into a filtration zone external of the main slurry body in the HCS reactor. The external filtration zone, conduit or vessel may be an extension or part of the downcomer.

By relatively high flow conditions is meant a velocity of greater than 5 ft./sec. and preferably greater than 10 ft./sec. Slurry flows of between 10–20 ft./sec. have been achieved in a gas reducing downcomer about 55 feet high and 3 inches in diameter, of the prior art type disclosed in U.S. Pat. No. 5,382,748. Build-up of catalyst particles as filter cake on the filter reduces the flow of the hydrocarbon liquid into the interior of the filter from which it is removed. In contrast to the prior art filtration processes, the relatively fast flow rate of the slurry past and across the filter surface in the practice of the invention carries the catalyst particles and any remaining gas bubbles with it. This produces relatively high shear flow and a scouring effect across the filtration surface, which minimizes catalyst particle build-up on the filter, thereby insuring greater liquid flow into the interior of the filter. The hydrocarbon liquid passes through the filter surface and into the interior of the filter as filtrate, which is removed from the filter and sent to a desired location such as storage, to product sales, further processing and upgrading into a variety of products, etc.. The slurry continues down through and out of the filtration zone and back into the main slurry body, which will typically be the reactive slurry in the HCS reactor. Filtrate passage through the filter is achieved by a pressure differential across the filtration surface. Reducing the gas content of the slurry also results in a greater liquid throughput through the filter. The slurry circulation from the reactor into an external filtration zone and back into the reactor occurs continuously by hydrostatic means, due to the density differences between the gas reduced slurry flowing past the filter and the lighter slurry in the reactor or other main slurry body. The filtration zone is either within the downcomer or in a downcomer fed vessel inside the slurry in the reactor, or outside the reactor. If the filtration zone is outside the slurry reactor, it is preferred that it have means, such as valves in the slurry circulation conduits connecting it to the reactor interior, which enable it to be isolated from the reactor. This isolation feature enables filter removal and replacement without having to take the HCS reactor off-line. Further, in a preferred embodiment the filter is removably secured in either or both the reactor or the filtration vessel, from the top thereof, for facile removal up and out of the top of the reactor or vessel through a nozzle or orifice, without having to drain the liquid from the reactor or vessel, or take it apart.

In one embodiment, the downcomer comprises a simple gas disengaging downcomer of the prior art, which produces the gas reduced slurry and feeds it into the filtration zone. In another embodiment, the downcomer comprises a gas and solids reducing downcomer which reduces both the gas and particulate solids content of the slurry, before it is fed into the downcomer conduit and into the filtration zone. Irrespective of whether the filtration zone is inside or outside of the reactor, in one embodiment the filter is located inside the downcomer itself. Circulation of the slurry from the reactor into and through the external vessel, conduit or zone and back into the reactor occurs by gravity due to hydrostatic heads due to the different slurry densities produced by the slurry gas reduction. In a still further embodiment, the filtration vessel, conduit or zone contains means for injecting a hydrogen rich gas into the slurry within, to avoid catalyst deactivation which can occur if all the hydrogen gas is removed or depleted from the slurry. While the invention is useful for removing liquid hydrocarbon product from a three phase slurry produced in a slurry hydrocarbon synthesis reaction, it is not intended to be limited to this particular embodiment.

With specific regard to a slurry HCS process for forming hydrocarbons, at least a portion of which are liquid at the reaction conditions, the invention comprises the steps of:

(a) reacting a synthesis gas comprising a mixture of $H_2$ and CO, in the presence of a solid, particulate hydrocarbon synthesis catalyst in a slurry body comprising said catalyst and gas bubbles in a hydrocarbon slurry liquid under reaction conditions effective to form hydrocarbons, at least a portion of which are liquid at said reaction conditions, wherein said slurry hydrocarbon liquid comprises said liquid hydrocarbons;

(b) passing a portion of said slurry from said slurry body through a gas disengaging zone immersed in said slurry body to form a gas reduced slurry;

(c) passing said gas reduced slurry from said gas disengaging zone through a downcomer and into a filtration zone under conditions of high flow;

(d) contacting said gas reduced slurry with filtration means in said filtration zone under said high flow conditions to separate a portion of said hydrocarbon liquid from said slurry as a filtrate and produce a hydrocarbon reduced slurry, and (e) passing said hydrocarbon reduced slurry back into said slurry body.

The hydrocarbon liquid filtrate is passed to storage, to upgrading by fractionation and conversion to more valuable products, sold neat, and the like. The filtration zone is either in the downcomer within the slurry or outside the reactor. The HCS reactor will typically be operating during filtration and the filtration may be continuous or intermittent. If the HCS reactor is on line and operating to produce hydrocarbons, passing the slurry through a gas disengaging downcomer to a filtration zone in the reactive slurry or outside it does not disturb or interfere with the HCS reaction. In yet another embodiment, a hydrogen containing gas is fed into the external filtration zone or vessel to prevent catalyst deactivation.

DETAILED DESCRIPTION

Figure 1:
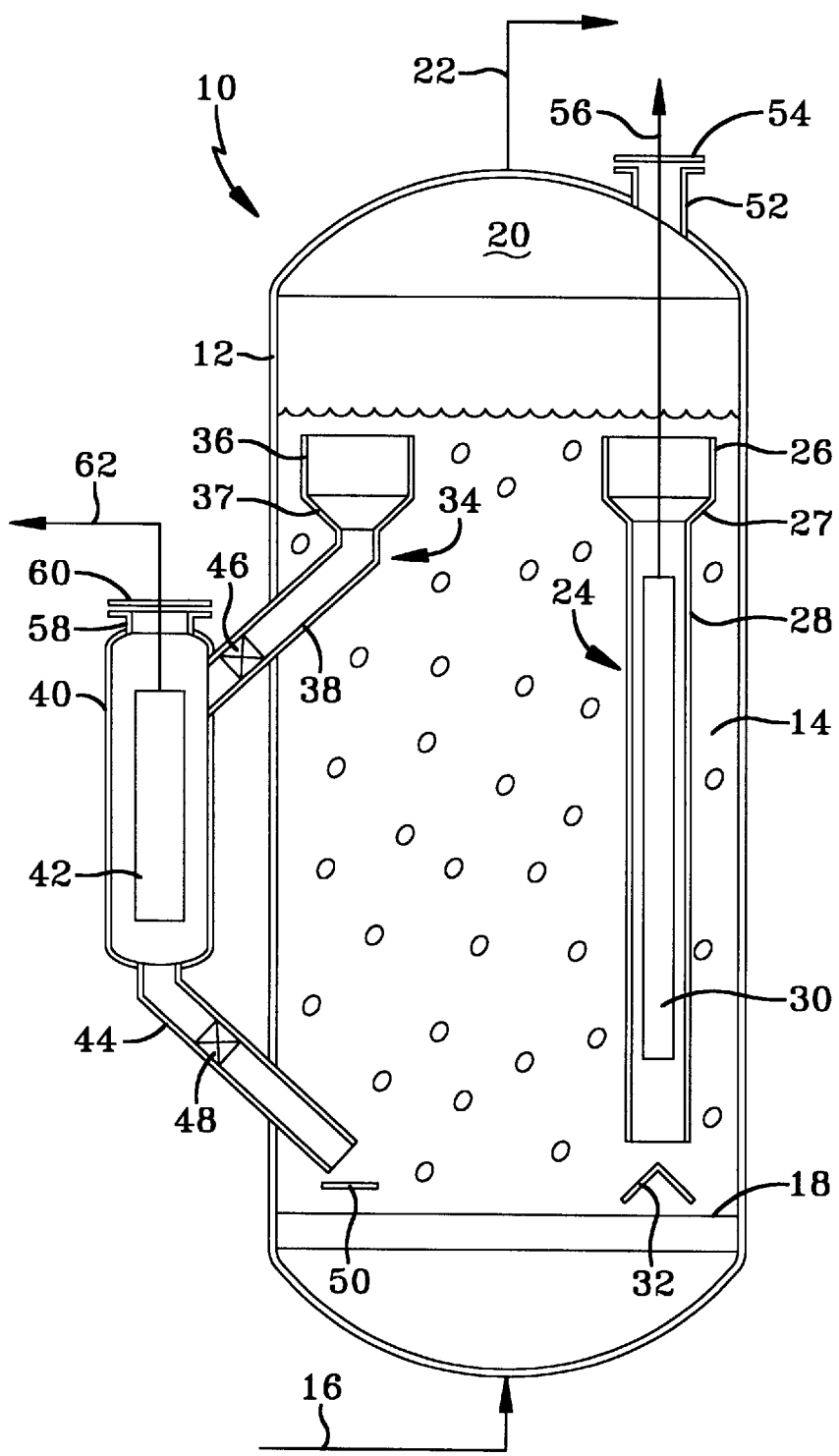
FIG. 1 is a cross-sectional schematic of an HCS reactor having both an internal and external filter fed by respective gas disengaging downcomers, useful in the practice of the invention.

In a Fischer-Tropsch slurry HCS process, a syngas comprising a mixture of $H_2$ and CO is bubbled up into a reactive slurry in which it is catalytically converted into hydrocarbons and preferably liquid hydrocarbons. The mole ratio of the hydrogen to the carbon monoxide may broadly range from about 0.5 to 4, but which is more typically within the range of from about 0.7 to 2.75 and preferably from about 0.7 to 2.5. The stoichiometric mole ratio for a Fischer-Tropsch HCS reaction is 2.0, but there are many reasons for using other than a stoichiometric ratio as those skilled in the art know and a discussion of which is beyond the scope of the present invention. In a slurry HCS process the mole ratio of the $H_2$ to CO is typically about 2.1/1. The slurry liquid in the reactor comprises the hydrocarbon products produced by the hydrocarbon synthesis reaction conditions which are liquid at the reaction conditions. A long standing problem has been the efficient separation and removal of the slurry hydrocarbon liquid product produced in the reactor from the relatively fine catalyst particles. The elevated temperature and pressure in the reactor and the waxy nature of the reaction hydrocarbon products make conventional particulate separation and filtration methods unsuitable for use in a slurry type hydrocarbon synthesis process. Thus, cyclone separation which has found such widespread use for separating catalyst particles from product vapors in cat cracking processes, is unsuitable for use with a waxy slurry, as are rotary and centrifuge filters.

While the temperature and pressure in the slurry can vary widely depending on the particular catalyst used and products desired, typical conditions effective to form hydrocarbons comprising mostly $C_{5+}$ paraffins, (e.g., $C_{5+}$–$C_{200}$) and preferably $C_{10+}$ paraffins, in a slurry HCS process employing a catalyst comprising a supported cobalt component include, for example, temperatures, pressures and hourly gas space velocities in the range of from about 320°–600° F., 80–600 psi and 100–40,000 V/hr/V, expressed as standard volumes of the gaseous CO and $H_2$ mixture (0° C., 1 atm) per hour per volume of catalyst, respectively. The slurry typically contains from about 10 wt. % to 70 wt. % catalyst solids, more typically from 30 wt. % to 60 wt. % and in some embodiments 40 wt. % to 55 wt. % is preferred. As mentioned above, the slurry liquid comprises the hydrocarbon products which are liquid at the reaction conditions, along with minor amounts of other components. While catalyst particle sizes may broadly range from as small as 1 to as large as 200 microns, a typical conventional Fe or supported iron catalyst will have a mean particle size of about 22 microns, while a catalyst comprising a catalytic metal such as cobalt composited with or supported on titania will typically have a mean particle size of about 63 microns. However, such catalysts will also include fine particles as small as 1 micron and the constant agitation and mixing of the catalyst particles in the slurry results in particle size reduction through attrition. This also produces fines having a particle size of from about 1 to 10 microns. It is not possible to filter out such fine particles with the massive and bulky wound wire prior art filters. This results in some of the catalyst particles being withdrawn through these filters along with the hydrocarbon liquid and these particles must be removed before the hydrocarbon liquid product is sent to upgrading. Further, removing the prior art bulky filters from the reactor invariably means shutting down the reactor and draining the liquid out of it so that a clogged or damaged filter can be replaced or repaired. The drained liquid has to be sent to hot storage so that it does not solidify and then returned back into to the reactor hot enough to enable continuation of the HCS reaction.

Referring to FIG. 1, a slurry reactor 10 comprises a hollow, cylindrical shell 12 containing a three phase HCS slurry 14 within. The slurry comprises solid catalyst particles and gas bubbles in a hydrocarbon liquid, wherein the hydrocarbon liquid comprises HCS hydrocarbon reaction products which are liquid at the synthesis reaction conditions. Gas inlet line 16 feeds a syngas into the reactor and up into the bottom of the slurry through suitable gas distribution means arranged across an otherwise gas and liquid impermeable tray 18 at the bottom of the slurry. The gas distribution means injects the gas up into the bottom of the slurry in which they rise as gas bubbles briefly indicated by the small circles. Gas reaction products of the HCS reaction and unreacted syngas escape the top of the slurry and collect in gas collection space 20 in the top of the reactor, from where they are removed via gas product line 22. A simple gas disengaging downcomer 24 similar to the prior art gas disengaging downcomer disclosed and claimed in U.S. Pat. No. 5,382,748 is shown fully immersed in the slurry. Downcomer 24 comprises an upwardly opening, hollow, cylindrical gas disengaging cup 26 which terminates at its bottom in a downwardly extending, hollow, cylindrical downcomer conduit or tube 28 open at both ends, which terminates near the bottom of the slurry as shown. A filter 30 is briefly illustrated as positioned within the interior of the downcomer. The filter may be a wire wound or other filter of the prior art. In a preferred embodiment (not shown) the filter 30 comprises one or more vertically arranged filter sections connected by a common filtrate collection conduit 56, wherein each section comprises one or more elongated, vertically disposed and hollow filter elements attached to and horizontally spaced across a manifold, with the manifolds connected to the filtrate conduit 56 for removing the hydrocarbon liquid from the slurry. The filter elements are preferably made if sintered metal having a pore size which permits the passage of the hydrocarbon liquid from the surrounding slurry into the interior of each element, but not the catalyst particles. The pressure on the downstream end on filtrate conduit 56 is less than that in the slurry, to provide the driving force for the liquid to pass through and into the interior of the filter. The hydrocarbon liquid filtrate is removed from the reactor via 56 and sent to a desired location or processing and upgrading by fractionation and/or one or more conversion operations to more valuable products, as set forth above under the Summary. A simple metal baffle, such as a cone 32, placed under the downcomer slurry exit prevents the uprising syngas bubbles from entering into the conduit and acting as a lift gas, which would reduce or prevent downflow of the slurry. As shown in the Figure, the bottom of the downcomer ends proximate the bottom of the slurry. This also enables the downcomer to assist in maintaining a more uniform vertical catalyst distribution in the slurry, in addition to passing the slurry across the filter under conditions of high liquid shear flow, to reduce catalyst particle build up on the filter as a filter cake which would reduce the hydrocarbon liquid product flow into the filter and out of the reactor. The downwardly flowing gas reduced slurry contacts the filter as it flows in a direction substantially parallel to the longitudinal axis of the filter. Downcomer 34 is similar to downcomer 24 and comprises an upwardly opening, hollow, cylindrical cup 36 which acts as a gas disengaging zone to remove gas bubbles from the slurry flowing down into it, to produce a slurry of greater density than that of the slurry in the surrounding slurry body 14. The gas disengaging cup 36 opens at its bottom into a hollow, cylindrical and downwardly extending downcomer conduit or tube 38. Downcomer 38 extends over laterally at an angle, out of the reactor and into filtration vessel 40 which contains a filter 42 inside similar to filter 30. The gas reduced slurry produced in the gas disengaging downcomer cup 36 passes down through the downcomer 38, into vessel 40, contacts the filter 42 under conditions of high liquid shear flow and passes out of 40 and back into the reactor via conduit 44. A simple baffle 50 placed under the exit of conduit 44 in the reactor prevents the uprising syngas bubbles from entering up into the conduit and filtration zone. Valves 46 and 48 enable the external filtration vessel to be isolated from the reactor for repair, maintenance and filter removal without disturbing the operation of the reactor and without the need for draining the reactor. They also assist in controlling the circulation or flow rate of the slurry from inside the reactor, to and through the external filtration zone and back into the reactor. This circulation is achieved hydrostatically due to density differences between the density of the slurry in the reactor and that of the gas reduced slurry formed in the gas disengaging cup of the downcomer. In this embodiment, the flow of the gas reduced slurry down through vessel 40 is in a direction substantially parallel to the longitudinal axis of the filter 42. In the embodiment shown, a nozzle 58 opens up out of the top of the vessel and is covered by a plate 60 which is fastened to the nozzle by suitable means, such as bolts. The filter is suspended in the vessel by line 62 or other means attached to the cover plate 60 (or other means) and sized so as to be vertically removable from the reactor up through nozzle 58 for repair and replacement. In one respect, both the vessel 40 and conduit 44 may be considered as an extension of the downcomer 38. Nozzle 52 extends up from the top of the reactor and is covered by cover plate 54 which is detachably attached to the top of the nozzle by bolts in a manner similar to that for cover plate 60. The filter 30 is suspended from plate 54 or other means, by means such as conduit 56 which is attached to the plate and the filter. The filter or both or the filter and downcomer are sized so as to be removable by lifting up out of nozzle 52 without having to drain the reactor. Thus, in both embodiments shown, the filter is removably secured in the filtration zone. Still further, the bottom of the filter in the downcomer or vessel bay be secured from horizontal movement by means such as a sleeve and rod combination, and the like, to permit vertical movement of the filter to adjust (thermal elongation and contraction) for temperature changes, while still permitting facile removal of the filter vertically upward.

Figure 2:
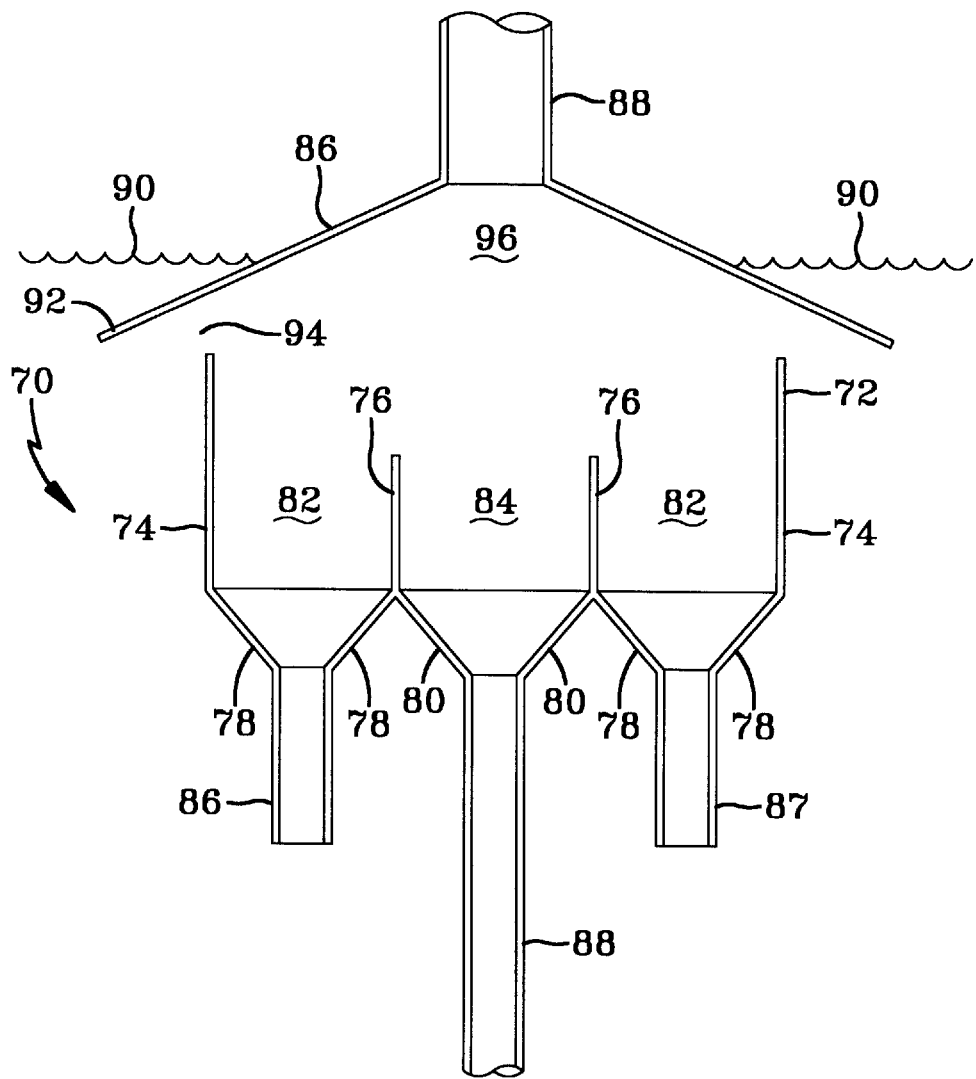
FIG. 2 is a simple cross-section, in schematic form, of a gas and solids reducing downcomer useful in the practice of the invention.

FIG. 2 schematically illustrates one embodiment of a gas and solids reducing downcomer 70, which comprises an outer, upwardly open cylindrical gas disengaging cup 72 having a vertical outer wall 74 and an inner cylindrical wall which, together with sloping bottom portions 78 and 80 respectively form outer and inner gas disengaging zones 82 and 84. A gas shield 86 in the form of a hollow cone having a hollow conduit 88 upwardly extending from its apex is positioned over the top of the downcomer. The downcomer is immersed in the slurry, only part of the top of which is illustrated as 90 and the bottom 92 of the gas baffle also extends into the slurry as shown. Peripheral space 94 between the bottom of the baffle and the top of the gas disengaging cup provides an annular flow path for the slurry to enter from the slurry body into the interior of the gas disengaging zones 82 and 84. Cylindrical wall 76 serves as an overflow weir. Slurry passes from the slurry body in which the downcomer is immersed and into the outer gas disengaging zone 82 in which gas bubbles and catalyst particles are disengaged to form a gas reduced and catalyst enriched slurry which is passed down downcomer conduits 86 and 87 which extend only a short distance down into the surrounding slurry body. Thus, a catalyst enriched slurry is formed and passed into the upper portion of the slurry body to assist in maintaining a more even vertical catalyst concentration in the slurry body. At the same time, and as a consequence of the removal of catalyst enriched slurry from the outer zone into the outer zone downcomers, a gas and catalyst particle or solids reduced slurry also formed in outer zone 82 passes over the top of the inner wall 76 and into the inner gas disengaging zone 84 in which more gas bubbles are disengaged to form a solids and further gas reduced slurry. This slurry passes down through inner downcomer conduit 88, from which it is passed across the filtration surface of the filter. Thus conduit 88 functions in the practice of the invention as either of downcomer conduits 28 and 38 in FIG. 1, with the difference being that a slurry reduced in both gas and solids is passed across the filter from downcomer 70. Thus, in this embodiment, the build up of a catalyst cake on the filter surface is further reduced due to the lower catalyst concentration in the slurry being filtered through it. As in the embodiment in FIG. 1, the bottom of downcomer conduit 88 may terminate proximate the bottom of the slurry to assist in maintaining a more uniform vertical catalyst concentration in the slurry body, by sending a solids reduced slurry down to the bottom where the catalyst concentration is the greatest. Irrespective of whether or not the downcomer feeds a solids reduced slurry down to the bottom of the slurry, the hydraulic pumping action of the slurry circulation of itself produces an upward lift to the slurry, which assists in keeping the catalyst particles dispersed in a more uniform vertical catalyst concentration. Studies with a two foot diameter gas disengaging cup on top of a three inch vertical downcomer have shown that, a slurry having a 60 volume % of gas bubbles passing through the cup disengages gas to form a slurry having about 30 volume % gas bubbles, which flows down the three inch downcomer tube at a rate of about 12 feet per second. The exact amount of gas disengaging and downflow velocity in this case depends on the length of the downcomer tube and the depth of the gas disengaging cup.

In a still further embodiment, a hydrogen rich gas is injected into the slurry in vessel 40 by means of gas line and suitable gas injection means (not shown). This embodiment is optional and the hydrogen rich gas, if used, is injected into the bottom of the vessel if needed to prevent deactivation of the catalyst particles therein. It has been found that if all of the hydrogen is removed from the slurry, the catalyst will slowly deactivate and this deactivation is not fully reversible. Consequently, if the catalyst particles are permitted to deactivate, the reactor must be taken off line, the slurry removed and the liquid separated from the catalyst, the catalyst processed to reactivate it, and the liquid and catalyst returned to the off line reactor which must be restarted to get it operating again.

In an HCS process, liquid and gaseous hydrocarbon products are formed by contacting a syngas comprising a mixture of $H_2$ and CO, under shifting or non-shifting conditions and preferably under non-shifting conditions in which little or no water gas shift reaction occurs, particularly when the catalytic metal comprises Co, Ru or mixture thereof Suitable Fischer-Tropsch reaction types of catalyst comprise, for example, one or more Group VIII catalytic metals such as Fe, Ni, Co, Ru and Re. In one embodiment the catalyst comprises catalytically effective amounts of Co and one or more of Re, Ru, Fe, Ni, Th, Zr, Hf, U, Mg and La on a suitable inorganic support material, preferably one which comprises one or more refractory metal oxides. Preferred supports for Co containing catalysts comprise titania, particularly when employing a slurry HCS process in which higher molecular weight, primarily paraffinic liquid hydrocarbon products are desired. Useful catalysts and their preparation are known and illustrative, but nonlimiting examples may be found, for example, in U.S. Pat. No. 4,568,663; 4,663,305; 4,542,122; 4,621,072 and 5,545,674.

The hydrocarbons produced by an HCS process according to the invention are typically upgraded to more valuable products, by subjecting all or a portion of the $C_{5+}$ hydrocarbons to fractionation and/or conversion. By conversion is meant one or more operations in which the molecular structure of at least a portion of the hydrocarbon is changed and includes both noncatalytic processing (e.g., steam cracking), and catalytic processing (e.g., catalytic cracking) in which a fraction is contacted with a suitable catalyst. If hydrogen is present as a reactant, such process steps are typically referred to as hydroconversion and include, for example, hydroisomerization, hydrocracking, hydrodewaxing, hydrorefining and the more severe hydrorefining referred to as hydrotreating, all conducted at conditions well known in the literature for hydroconversion of hydrocarbon feeds, including hydrocarbon feeds rich in paraffins. Illustrative, but nonlimiting examples of more valuable products formed by conversion include one or more of a synthetic crude oil, liquid fuel, olefins, solvents, lubricating, industrial or medicinal oil, waxy hydrocarbons, nitrogen and oxygen containing compounds, and the like. Liquid fuel includes one or more of motor gasoline, diesel fuel, jet fuel, and kerosene, while lubricating oil includes, for example, automotive, jet, turbine and metal working oils. Industrial oil includes well drilling fluids, agricultural oils, heat transfer fluids and the like.

It is understood that various other embodiments and modifications in the practice of the invention will be apparent to, and can be readily made by, those skilled in the art without departing from the scope and spirit of the invention described above. Accordingly, it is not intended that the scope of the claims appended hereto be limited to the exact description set forth above, but rather that the claims be construed as encompassing all of the features of patentable novelty which reside in the present invention, including all the features and embodiments which would be treated as equivalents thereof by those skilled in the art to which the invention pertains.

What is claimed:

1. A slurry hydrocarbon synthesis process for forming hydrocarbons comprising:
   (a) reacting a synthesis gas comprising a mixture of $H_2$ and CO, in the presence of a solid, particulate hydrocarbon synthesis catalyst in a slurry body comprising said catalyst and gas bubbles in a hydrocarbon slurry liquid under reaction conditions effective to form hydrocarbons, at least a portion of which are liquid at said reaction conditions, wherein said slurry hydrocarbon liquid comprises said liquid hydrocarbons;
   (b) passing a portion of said slurry from said slurry body through a gas disengaging zone immersed in said slurry body to form a gas reduced slurry;
   (c) passing said gas reduced slurry from said gas disengaging zone through a downcomer and into a filtration zone under conditions of high flow;
   (d) contacting said gas reduced slurry with filtration means in said filtration zone under said high flow conditions to separate a portion of said hydrocarbon liquid from said slurry as a filtrate and produce a hydrocarbon reduced slurry, and
   (e) passing hydrocarbon reduced slurry back into said slurry body.

2. A process according to claim 1 wherein said slurry body is in a hydrocarbon synthesis reactor.

3. A process according to claim 2 wherein said gas reduced slurry in produced in a gas disengaging downcomer.

4. A process according to claim 2 wherein a portion of said slurry body is passed out of said reactor and wherein said gas reduced slurry is formed external of said reactor.

5. A process according to claim 1, wherein in step (b) said slurry is also passed through a solids reducing zone to produce a gas and solids reduced slurry which is passed through said filtration zone under said high liquid shear flow conditions and back into said slurry body.

6. A process according to claim 5 wherein said gas and solids reduced slurry is produced in a gas and solids reducing downcomer.

7. A process according to claim 2 wherein said filtration zone is external of said reactor.

8. A process according to claim 3 wherein said filtration means is vertically upwardly removable from said filtration zone.

9. A process according to claim 8 wherein said filtration zone is within said slurry body.

10. A process according to claim 9 wherein said filtration zone is within said downcomer immersed in said slurry body.

11. A process according to claim 1 wherein at least a portion of said filtrate is subjected to conversion.

12. A process according to claim 11 wherein the conversion is non-catalytic.

13. A process according to claim 11 wherein the conversion is catalytic.

14. A process according to claim 13 wherein hydrogen is present in the catalytic conversion.

15. A process according to claim 14 wherein the catalytic conversion is hydroisomerization.

* * * * *